United States Patent
Narimatsu et al.

(10) Patent No.: US 6,786,872 B2
(45) Date of Patent: Sep. 7, 2004

(54) AUGMENTATION-INDEX MEASURING APPARATUS

(75) Inventors: Kiyoyuki Narimatsu, Komaki (JP); Toshihiko Ogura, Komaki (JP); Akira Tampo, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 83 days.

(21) Appl. No.: 10/351,389

(22) Filed: Jan. 27, 2003

(65) Prior Publication Data

US 2003/0199773 A1 Oct. 23, 2003

(30) Foreign Application Priority Data

Apr. 17, 2002 (JP) ........................................ 2002-115183

(51) Int. Cl.⁷ .................................................. A61B 5/02

(52) U.S. Cl. ........................................ 600/490; 600/494

(58) Field of Search .......................... 600/490, 492–496, 600/500–503, 485

(56) References Cited

U.S. PATENT DOCUMENTS

| 5,265,011 A | 11/1993 | O'Rourke |
| 5,913,826 A | 6/1999 | Blank |
| 6,612,993 B2 * | 9/2003 | Narimatsu ................ 600/500 |

FOREIGN PATENT DOCUMENTS

| EP | 1 161 920 A2 | 12/2001 |
| EP | 1 340 453 A2 | 9/2003 |
| WO | WO 02/05726 A2 | 1/2002 |

* cited by examiner

*Primary Examiner*—Mary Beth Jones
*Assistant Examiner*—Navin Natnithithadha
(74) *Attorney, Agent, or Firm*—Oliff & Berridge, PLC (57) ABSTRACT

An augmentation-index measuring apparatus including a cuff which is adapted to be worn on a portion of a living subject to press the portion, an augmentation-index determining device for determining an augmentation index of the subject based on a cuff pulse wave obtained from the cuff, and a preliminary pressing device for preliminarily pressing, before the cuff pulse wave is obtained, for the determination of the augmentation index, from the cuff having a pulse-wave detection pressure, the portion of the subject using the cuff having a pressure higher than the pulse-wave detection pressure.

7 Claims, 6 Drawing Sheets

AUGMENTATION-INDEX MEASURING APPARATUS

BACKGROUND OF THE INVENTION

1. Field of the Invention

The present invention relates to an augmentation-index measuring apparatus which measures an augmentation index based on a cuff pulse wave occurring to a cuff worn on a living, subject.

2. Related Art Statement

Augmentation index, generally known as AI, indicates, e.g., a proportion of a reflected-wave component of a pulse wave to an incident-wave component of the same, and is used to evaluate compliance of aorta. As the compliance of aorta increases, the reflected-wave component decreases and, as the compliance of aorta decreases, the reflected-wave component increases. More specifically described, if wall of aorta hardens, a reflected-wave component contained in the form of pulse wave obtained from the aorta increases. Thus, augmentation index reflects arteriosclerosis, and can be used as an index for inspecting arteriosclerosis.

As described above, augmentation index indicates a proportion of a reflected-wave component of a pulse wave to an incident-wave component of the same, but it is difficult to separate a pulse wave detected (hereinafter, referred to as a detected pulse wave) into its incident-wave component and reflected-wave component. Hence, an augmentation index may be determined as follows: First, a detected pulse wave is analyzed to identify respective peak points of an incident-wave component and a reflected-wave component of the pulse wave. Then, the augmentation index is calculated by dividing a difference between a magnitude of the pulse wave at the time of occurrence of the peak of the incident-wave component and a magnitude of the pulse wave at the time of occurrence of the peak of the reflected-wave component, by a pulse pressure of the pulse wave. In addition, the peak of the incident-wave component may be determined as an inflection point or a local maximum point between a rising point of the detected pulse wave and a peak of the same; and the peak of the reflected-wave component may be determined as the first local maximum point following the peak of the incident-wave component.

Since augmentation index is used to evaluate compliance of aorta as described above, it is a clinical practice to non-invasively detect a pulse wave from a carotid artery that is the nearest to the aorta and determine an augmentation index based on the carotid pulse wave. However, first, it needs adequate skill to wear, at an appropriate position, a carotid-pulse-wave sensor for detecting a carotid pulse wave and, second, it is needed to use or employ the carotid-pulse-wave sensor. Thus, there is a need to easily measure an augmentation index using a cuff pulse wave which is detected from a cuff worn on, e.g., an upper arm of a living subject for measuring a blood pressure of the subject.

However, the cuff pulse wave occurring to the cuff pressing the portion of the living subject suffers the problem of low degree of reproducibility or stability, and accordingly the augmentation index obtained from the cuff pulse wave suffers the same problem and cannot enjoy high accuracy of measurement.

SUMMARY OF THE INVENTION

It is therefore an object of the present invention to provide an augmentation-index measuring apparatus which can measure an accurate augmentation index based on a cuff pulse wave.

The Inventors have performed extensive studies and found that since the skin and subcutaneous tissue of a portion of a living subject that is pressed by a cuff being wound therearound, e.g., the skin and subcutaneous tissue of an upper arm contain a high proportion of water, the portion is deformed by the pressing of the cuff in such a manner that the thickness of skin and subcutaneous tissue decreases, and that this is the cause of changing a relationship between the cuff and an artery located under the cuff and thereby time-wise changing the condition under which a cuff pulse wave is detected.

The above object has been achieved by the present invention. According to a first aspect of the present invention, there is provided an augmentation-index measuring apparatus comprising a cuff which is adapted to be worn on a portion of a living subject to press the portion; an augmentation-index determining means for determining an augmentation index of the subject based on a cuff pulse wave obtained from the cuff and a preliminary pressing means for preliminarily pressing, before the cuff pulse wave is obtained, for the determination of the augmentation index, from the cuff having a pulse-wave detection pressure, the portion of the subject using the cuff having a pressure higher than the pulse-wave detection pressure.

According to this aspect of the invention, the preliminary pressing means preliminarily presses, before the cuff pulse wave is obtained for the determination of the augmentation index, the portion of the subject using the cuff having the pressure higher than the pulse-wave detection pressure used to press the portion for obtaining the cuff pulse wave. Therefore, the water contained in the skin and subcutaneous tissue of the portion being pressed by the cuff is squeezed out of the portion being pressed, so that the thickness of skin and subcutaneous tissue decreases to a value corresponding to the pressing. Since a cuff pulse wave is obtained in this state, the cuff pulse wave can enjoy a high stability, and an augmentation index determined based on the cuff pulse wave can enjoy a high accuracy.

According to a preferred feature of the first aspect of the present invention, the preliminary pressing means preliminarily presses the portion of the subject, within a sufficiently shorter time period than a time period in which the skin and subcutaneous tissue of the portion pressed by the means are restored to their initial state. For example, the preliminary pressing means finishes the preliminary pressing of the portion of the subject within several minutes (e.g., five or six minutes), more preferably, several tens of seconds (e.g., fifty or sixty seconds) before commencement of the obtaining of the cuff pulse wave for the determination of the augmentation index.

According to another feature of the first aspect of the present invention, the preliminary pressing means preliminarily presses the portion of the subject by carrying out a predetermined number of blood-pressure measurements using the cuff. According to this feature, the augmentation index can be obtained simultaneously with the blood-pressure measurement or measurements.

According to another feature of the first aspect of the present invention, the preliminary pressing means preliminarily presses the portion of the subject for a predetermined preliminary pressing time before the cuff pulse wave is obtained for the determination of the augmentation index. According to this feature, the portion of the subject is preliminarily pressed for the predetermined preliminary-pressing time, and accordingly the water contained in the skin and subcutaneous tissue of the portion being pressed by the cuff is squeezed out of the portion being pressed, so that the thickness of skin and subcutaneous tissue decreases to a value corresponding to the pressing of the cuff and, in this state, the cuff pulse wave is obtained for the determination of augmentation index.

According to another feature of the first aspect of the present invention, the preliminary pressing means preliminarily presses the portion of the subject with a pressure higher than a systolic blood pressure of the subject. According to this feature, the portion of the subject is preliminarily pressed with the pressure higher than the systolic blood pressure of the subject and accordingly the water contained in the skin and subcutaneous tissue of the portion being pressed by the cuff is squeezed out of the portion being pressed, so that the thickness of skin and subcutaneous tissue decreases to a value corresponding to the pressing of the cuff and, in this state, the cuff pulse wave is obtained for the determination of augmentation index.

According to another feature of the first aspect of the present invention, the augmentation-index measuring apparatus further comprises a cuff-pressure changing device which changes, for a blood-pressure measurement, the pressure of the cuff from a pressure higher than a systolic blood pressure of the subject to a pressure lower than a diastolic blood pressure of the subject, and the cuff pulse wave is obtained, immediately after the blood-pressure measurement, from the cuff having a pressure lower than the diastolic blood pressure of the subject obtained from the blood-pressure measurement. According to this feature, the augmentation index can be obtained simultaneously with the blood-pressure measurement.

A second aspect of the present invention is directed to use of the augmentation-index measuring apparatus according to the first aspect of the invention, for inspecting a degree of arteriosclerosis of the subject. That is, the augmentation-index measuring apparatus can be used as an arteriosclerosis-degree inspecting apparatus for inspecting the degree of arteriosclerosis of the subject based on the augmentation index determined by the augmentation-index determining means.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
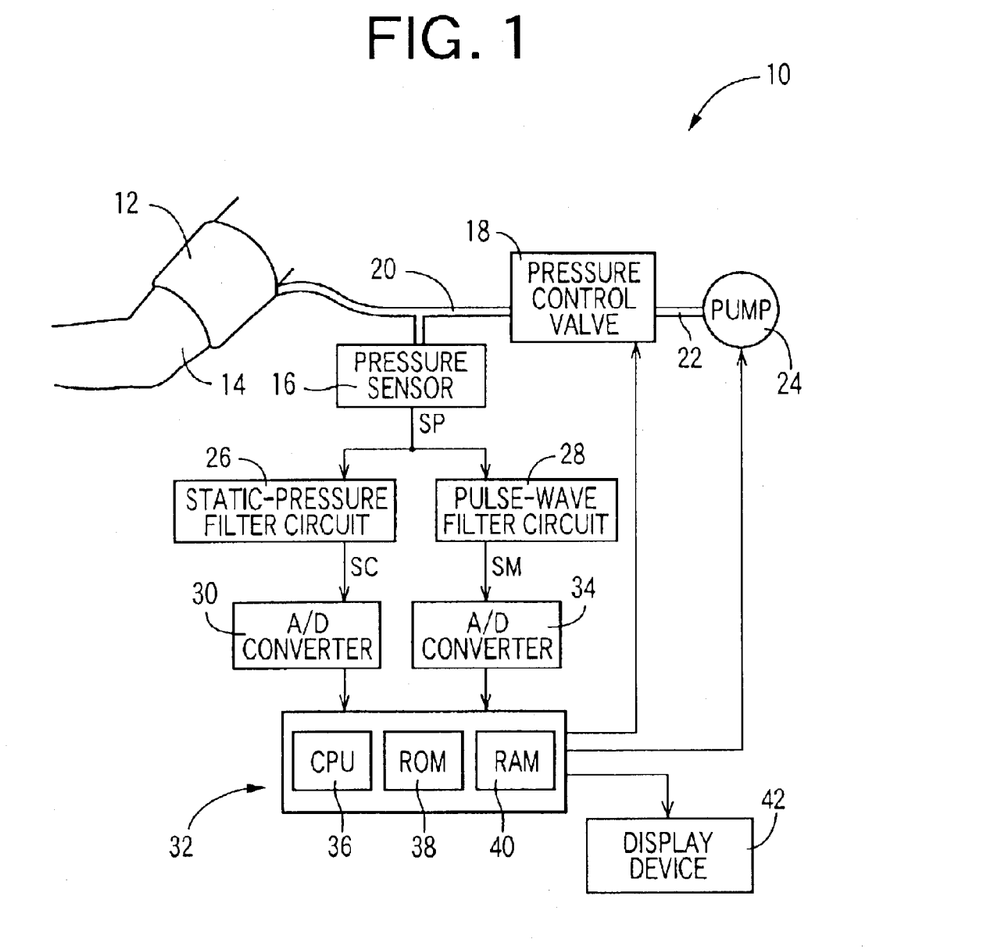
FIG. 1 is a diagrammatic view showing a circuitry of a blood-pressure measuring apparatus having an augmentation-index determining function, to which the present invention is applied.

Hereinafter, there will be described an embodiment of the present invention in detail by reference to the drawings. FIG. 1 is a diagrammatic view showing a circuitry of a blood-pressure measuring apparatus 10 to which the present invention is applied and which has an augmentation-index measuring function. The present blood-pressure measuring apparatus 10 can also be used as an arteriosclerosis inspecting apparatus.

In FIG. 1, reference numeral 12 designates an inflatable cuff which includes a belt-like cloth bag and a rubber bag accommodated in the cloth bag and which is adapted to be wound around an upper portion 14 of a living subject. The cuff 12 is connected via a piping 20 to a pressure sensor 16 and a pressure control valve 18. The pressure control valve 18 is connected via a piping 22 to an air pump 24. The pressure control valve 18 adjusts a pressure of a pressurized air supplied from the air pump 24, and supplies the pressure-adjusted air to the cuff 12, or discharges the pressurized air from the cuff 12, so as to control an air pressure in the cuff 12.

The pressure sensor 16 detects the air pressure in the cuff 12, and supplies a pressure signal, SP, representing the detected air pressure, to a static-pressure filter circuit 26 and a pulse-wave filter circuit (i.e., a pulse-wave filter device) 28. The static-pressure filter circuit 26 includes a low-pass filter which extracts, from the pressure signal SP, a cuff-pressure signal, SC, representing a static component of the detected air pressure, i.e., a pressing pressure of the cuff 12 (hereinafter, referred to as the cuff pressure, Pc). The filter circuit 26 supplies the cuff-pressure signal SC to an electronic control device 32 via an A/D (analog-to-digital) converter 30. The pulse-wave filter circuit 28 includes a band-pass filter that permits passing of signals having frequencies of from 1 to 30 Hz and thereby extracts, from the pressure signal SP, a cuff-pulse-wave signal, SM, representing a cuff pulse wave as an oscillatory component of the detected air pressure. The filter circuit 28 supplies the cuff-pulse-wave signal SM to the control device 32 via an A/D converter 34. The cuff pulse wave represented by the cuff-pulse-wave signal SM is a pressure oscillation transmitted from an artery of the subject to the cuff 12 and, since this artery is a brachial artery, the cuff pulse wave is a brachial pulse wave.

The control device 32 is provided by a so-called microcomputer including a CPU (central processing unit) 36, a ROM (read only memory) 38, a RAM (random access memory) 40, and an I/O (input-and-output) port, not shown. The CPU 36 processes signals according to the control programs pre-stored in the ROM 38 by utilizing the temporary-storage function of the RAM 40, and supplies drive signals via the I/O port to the air pump 24 and the pressure control valve 18 so as to control the cuff pressure Pc. Moreover, the CPU 36 has various functions shown in detail in FIG. 2 for determining an augmentation index AI of the subject, and controls what is displayed by a display device 42.

Figure 2:
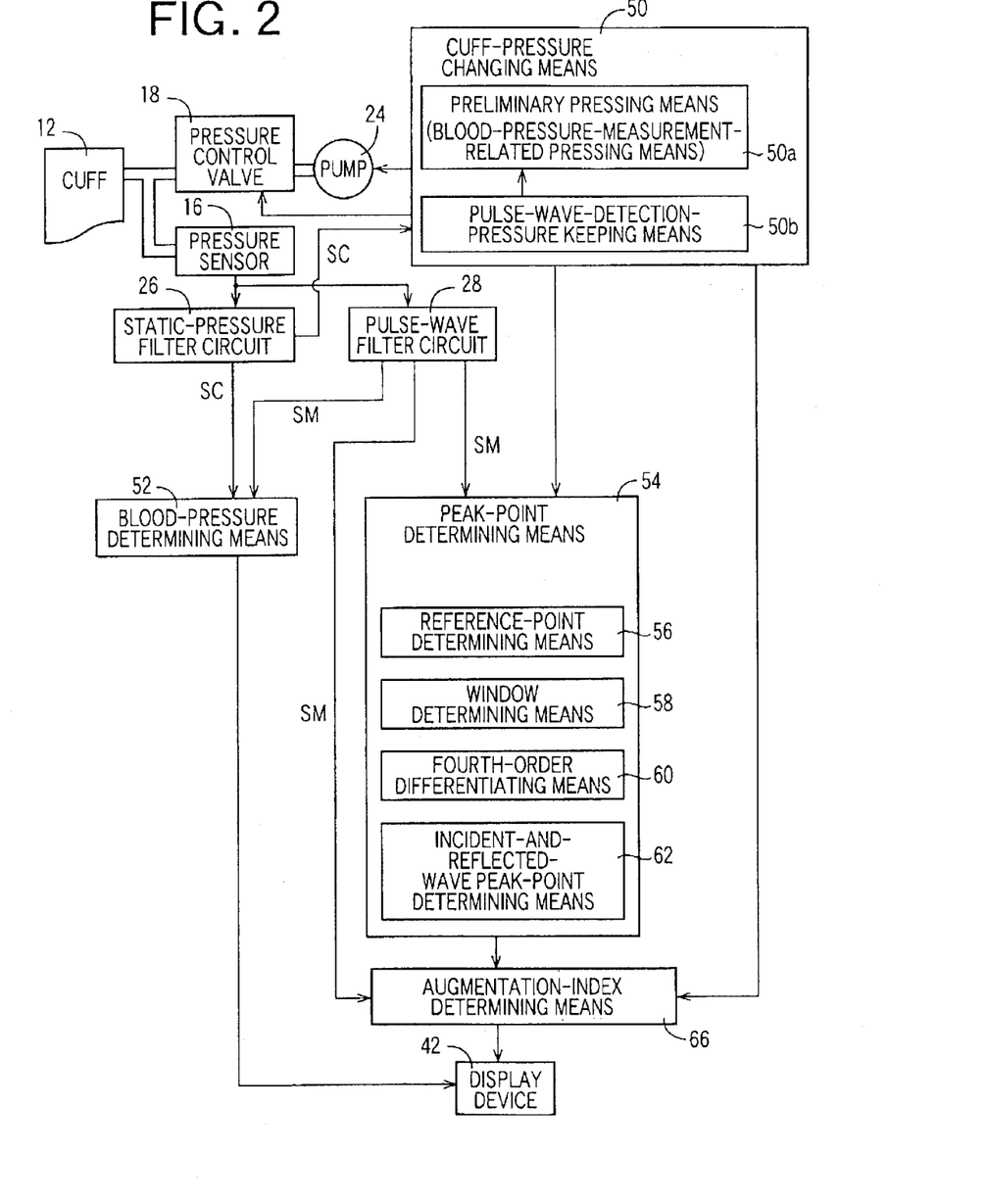
FIG. 2 is a block diagram for explaining essential control functions of an electronic control device of the blood-pressure measuring apparatus having the augmentation-index determining function, shown in FIG. 1.

FIG. 2 is a block diagram for explaining essential control functions of the control device 32 of the blood-pressure measuring apparatus 10.

A cuff-pressure changing means 50 operates, based on the cuff-pressure signal SC supplied from the static-pressure filter circuit 26, the pressure control valve 18 and the air pump 24 so as to change the cuff pressure Pc. Thus, the static-pressure filter circuit 26, the pressure control valve 18, the air pump 24, and the cuff-pressure changing means 50 cooperate with one another to provide a cuff-pressure changing device. The cuff-pressure changing means 50 includes a preliminary pressing means (a blood-pressure-measurement-related pressing means) 50a for preliminarily pressing, before a cuff-pulse-wave signal SM is obtained for the measurement of augmentation index AI, the upper arm 14 with the cuff 12 being wound, i.e., with a pressure sufficiently higher than a pulse-wave detection pressure, e.g., a pressure higher than a systolic blood pressure $BP_{SYS}$ of the subject; and a pulse-wave-detection-pressure keeping means 50b for keeping, immediately after the preliminary pressing of the upper arm 14, the pressure of the cuff 12 to the pulse-wave detection pressure pre-determined to be lower than a diastolic blood pressure $BP_{DIA}$ of the subject. More specifically described, the cuff-pressure changing means 50 quickly increases the cuff pressure Pc from the pulse-wave detection pressure to a target pressure value (e.g., 180 mmHg) pre-determined to be higher than the systolic blood pressure $BP_{SYS}$ of the upper arm 14, and then slowly decreases the cuff pressure Pc at a prescribed rate of from 2 to 3 mmHg/sec. In addition, after a blood-pressure determining means 52, described later, determines a diastolic blood pressure $BP_{DIA}$ of the subject, the cuff-pressure changing means 50 keeps, for a time corresponding to not less than one heartbeat of the subject, the cuff pressure Pc to the pulse-wave detection pressure predetermined based on a mean blood pressure $BP_{MEAN}$ or the diastolic blood pressure $BP_{DIA}$ of the subject, so as to obtain a cuff pulse wave. If the above-indicated pulse-wave detection pressure is higher than the diastolic blood pressure $BP_{DIA}$ of the subject, the cuff pulse wave extracted by the pulse-wave filter circuit 28 is deformed. In particular, if pulse-wave detection pressure is higher than the mean blood pressure $BP_{MEAN}$ of the subject, the cuff pulse wave is so largely deformed that an accurate augmentation index AI cannot be determined. Thus, the pulse-wave detection pressure is preferably lower than the mean blood pressure $BP_{MEAN}$ of the subject, more preferably lower than the diastolic blood pressure $BP_{DIA}$ of the subject, for example, a pressure of from 50 mmHg to 60 mmHg. However, if the cuff pressure Pc is too low, the cuff pulse wave detected is too small to determine an accurate augmentation index AI. Thus, the pulse-wave detection pressure is pre-determined at a value that assures that a cuff pulse wave having a sufficiently great magnitude is detected.

The blood-pressure determining means 52 determines, based on the change of respective amplitudes of a plurality of heartbeat-synchronous pulses of the brachial pulse wave represented by the cuff-pulse-wave signal SM continuously obtained during the slow decreasing of the cuff pressure Pc under the control of the cuff-pressure changing means 50, a systolic blood pressure $BP_{SYS}$, a mean blood pressure $BP_{MEAN}$, and a diastolic blood pressure $BP_{DIA}$ of the subject, according to well-known oscillometric method. In addition, the determining means 52 operates the display device 42 to display the thus determined systolic blood pressure $BP_{SYS}$, etc.

Figure 3:
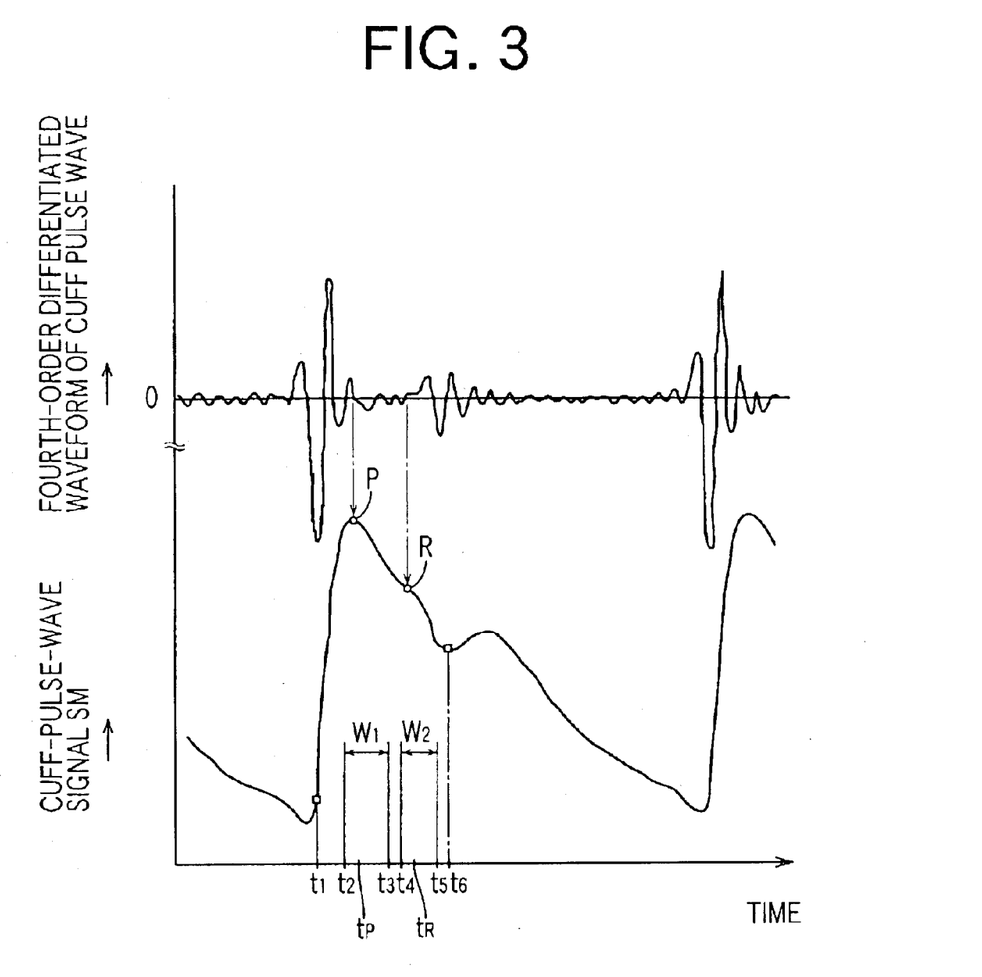
FIG. 3 is a time chart showing a relationship among a cuff pulse wave, a fourth-order-differentiated waveform, a rising-point window $W_1$, a notch-point window $W_2$, an incident-wave peak point P, and a reflected-wave peak point R that are obtained or determined by the control device shown in FIG. 2.
Figure 4:
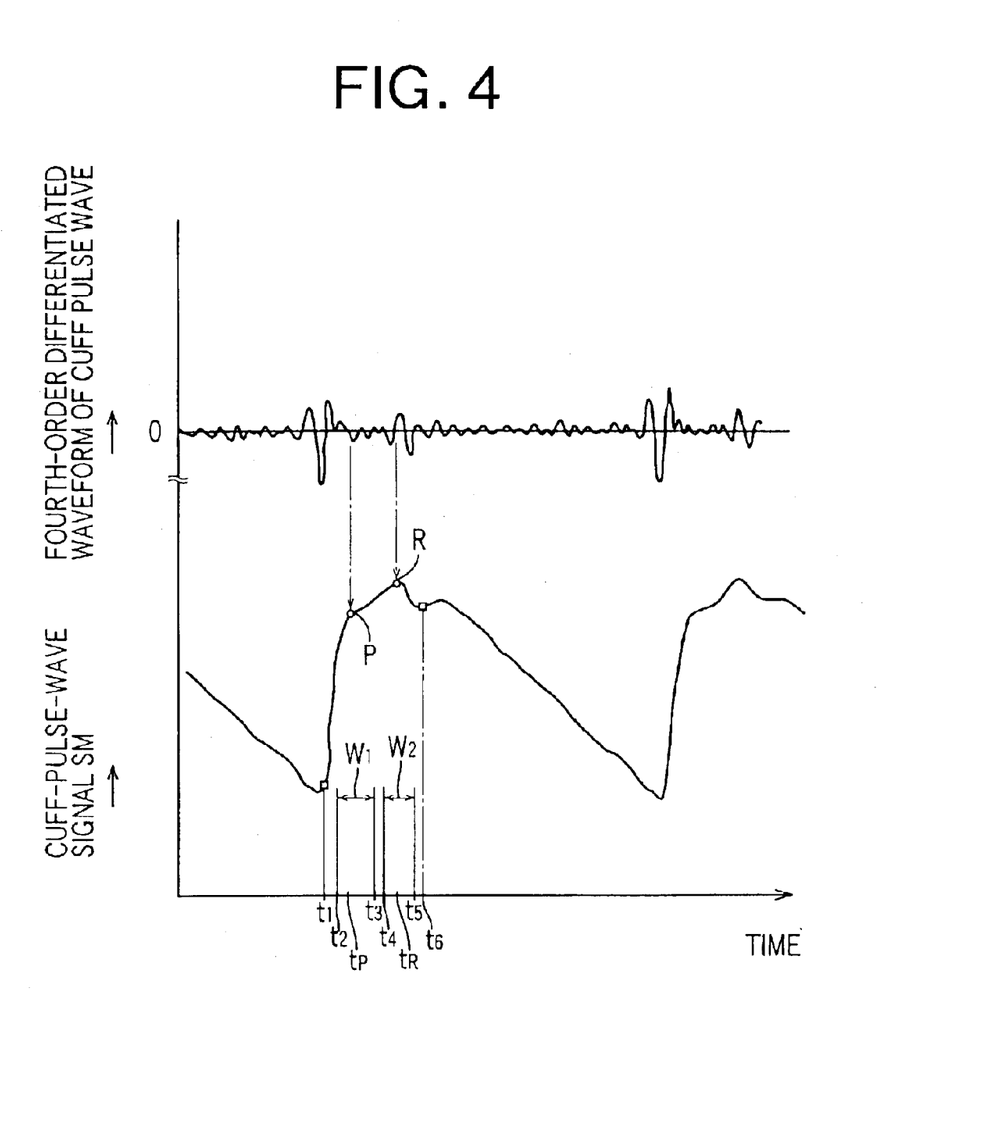
FIG. 4 is a time chart showing a relationship among a cuff pulse wave having a different waveform than that of the cuff pulse wave shown in FIG. 3, a fourth-order-differentiated waveform, a rising-point window $W_1$, a notch-point window $W_2$, an incident-wave peak point P, and a reflected-wave peak point R.

A peak-point determining means 54 subjects, to fourth-order differentiation, the cuff-pulse-wave signal SM obtained from the cuff 12 in the state in which the cuff pressure Pc is kept at the pulse-wave detection pressure, and determines, based on the thus obtained fourth-order-differentiated waveform of the signal SM, more specifically, zero-crossing points of the differentiated waveform, a peak point P of an incident-wave component of the signal SM, a time $t_P$ of occurrence of the point P, a peak point R of a reflected-wave component of the signal SM, and a time $t_R$ of occurrence of the point R. FIGS. 3 and 4 show two cuff-pulse-wave signals SM having different waveforms, respectively, and their respective fourth-order-differentiated waveforms, and each of the FIGS. 3 and 4 shows the corresponding one signal SM and its differentiated waveform along a common time axis, and a peak point P of an incident-wave component of the signal SM, a time $t_P$ of occurrence of the point P, a peak point R of a reflected-wave component of the signal SM, and a time $t_R$ of occurrence of the point R.

The peak-point determining means 54 includes a reference-point determining means 56 for determining, based on each of the respective forms of the two cuff pulse waves obtained by the cuff-pulse-wave obtaining means 53, reference points on the each cuff pulse wave, i.e., a rising point $t_1$ and a notch point $t_6$; a window determining means 58 for determining a rising-point window (i.e., a time gate) $W_1$ that starts and ends at a time $t_2$ and a time $t_3$, respectively, that are subsequent by respective prescribed times to the rising point $t_1$, and additionally determining a notch-point window (a time gate) $W_2$ that starts and ends at a time $t_4$ and a time $t_5$, respectively, that are prior by respective prescribed times to the notch point $t_6$; a fourth-order differentiating means 60 for fourth-order differentiating, i.e., four times differentiating the each cuff pulse wave obtained by the cuff-pulse-wave obtaining means 53; and an incident-and-reflected-wave peak-point determining means 62 for determining, based on two zero-crossing points of the thus obtained fourth-order differentiated waveform that fall within the rising-point window $W_1$ and the notch-point window $W_2$, respectively, a peak point P of an incident-wave component of the cuff pulse wave, a time of occurrence of the peak point P, a peak point R of a reflected-wave component of the cuff pulse wave, and a time $t_R$ of occurrence of the point R. The reference-point determining means 56 determines, as a rising point $t_1$, a point that is subsequent to a local minimum point of a heartbeat-synchronous pulse of the cuff pulse wave and has a magnitude equal to a predetermined proportion, e.g., one tenth, of an amplitude between the minimum point and a maximum point of the heartbeat-synchronous pulse, and additionally determines, as a notch point $t_6$, the first local minimum point, or the first inflection point, subsequent to the maximum point. The incident-and-reflected-wave peak-point determining means 62 determines, as a peak point $t_P$ of an incident-wave component, a zero-crossing point that has a pre-determined position as counted from the start point of the rising-point window $W_1$, e.g., the first zero-crossing point falling in the rising-point window $W_1$, and crosses zero in a direction from a positive area to a negative area; and additionally determines, as a peak point $t_R$ of a reflected-wave component, a zero-crossing point that has a pre-determined position as counted from the start point of the notch-point window $W_2$, e.g., the first zero-crossing point falling in the notch-point window $W_2$, and crosses zero in a direction from the negative area to the positive area. The respective times from the rising point $t_1$ to the start and end points of the rising-point window $W_1$ and the respective times from the notch point $t_6$ to the start and end points of the notch-point window $W_2$, employed by the window determining means 58, are experimentally determined in advance so that the peak points $t_P$, $t_R$ can fall in the widows $W_1$, $W_2$, respectively.

An augmentation-index determining means 66 first determines a maximum magnitude and a minimum magnitude of a heartbeat-synchronous pulse of the cuff-pulse-wave signal SM obtained from the cuff 12 kept at the pulse-wave detection pressure, and additionally determines, as a pulse pressure (i.e., a maximum amplitude) PP of the cuff pulse wave, a difference between the maximum and minimum magnitudes. Moreover, the augmentation-index determining means 66 determines, according to a relationship represented by the following Expression 1, an augmentation index AI based on the pulse pressure PP and a difference $\Delta P(=b-a)$ obtained by subtracting a magnitude, a, of the cuff pulse wave at the time of occurrence of peak point $t_P$ of the incident-wave component from a magnitude, b, of the cuff pulse wave at the time of occurrence of peak point $t_R$ of the reflected-wave component, and operates the display device 42 to display the thus determined augmentation index AI.

$$AI=(\Delta P/PP)\times 100(\%) \quad \text{(Expression 1)}$$

Figure 5:
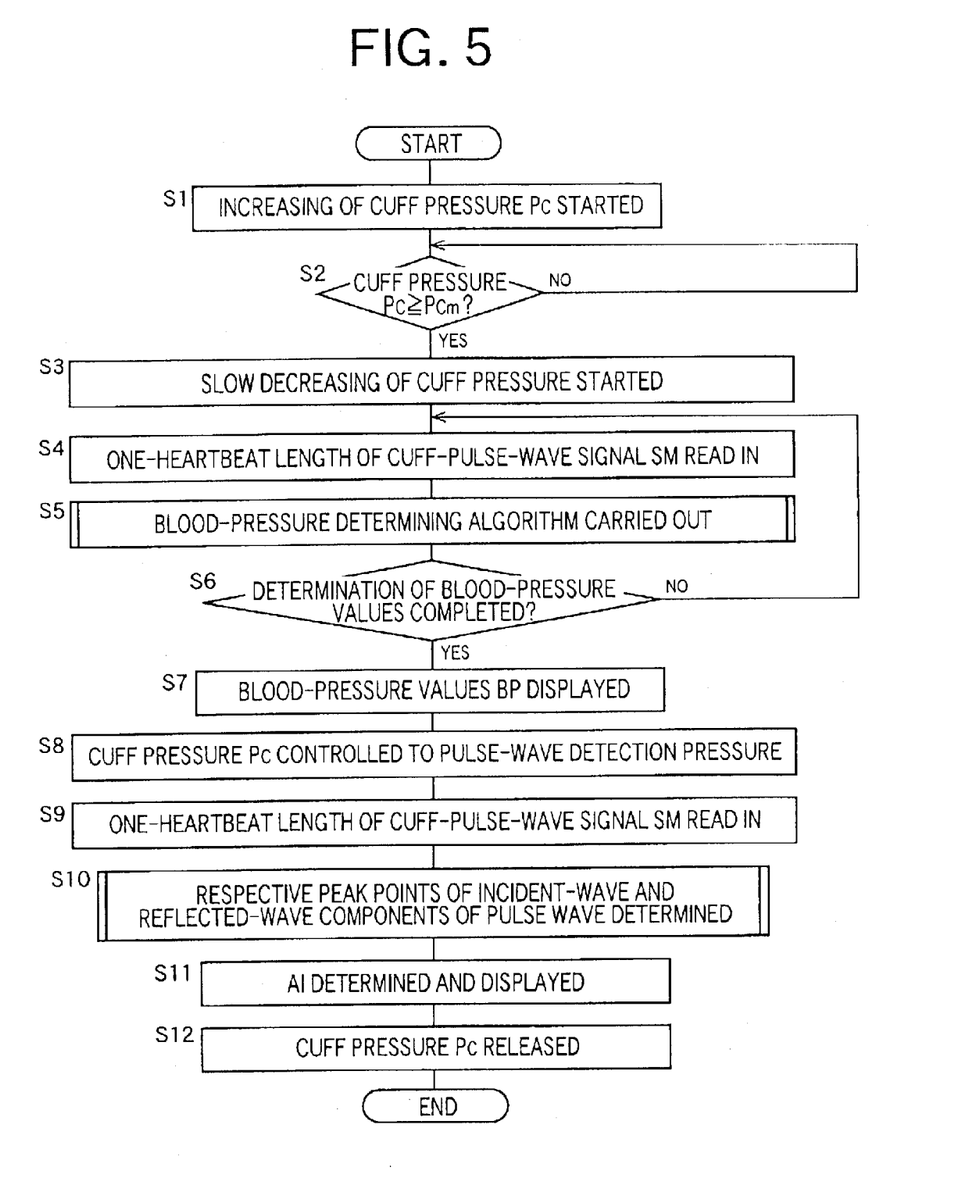
FIG. 5 is a flow chart for explaining the essential control functions of the electronic control device of the blood-pressure measuring apparatus having the augmentation-index determining function, shown in FIG. 1.
Figure 6:
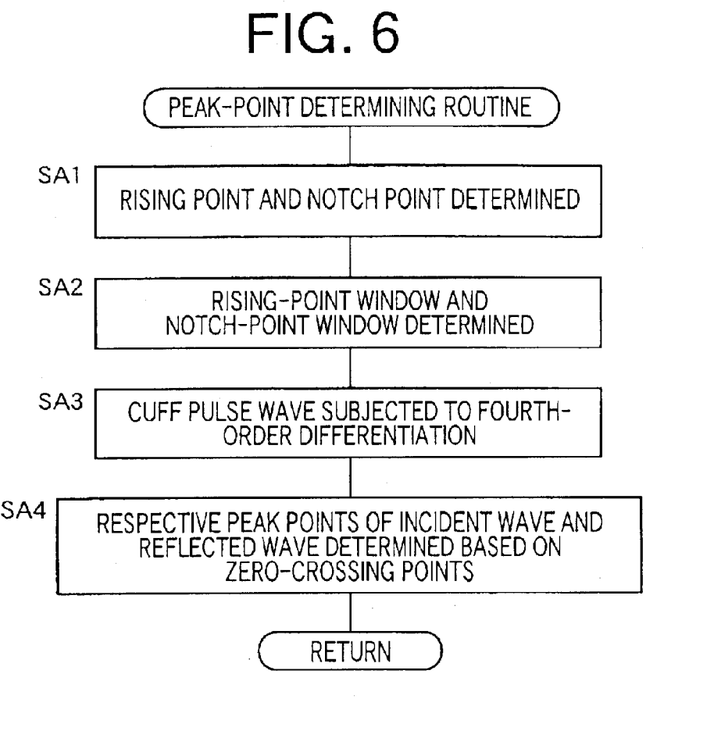
FIG. 6 is a flow chart for explaining a peak-point determining routine employed in the flow chart shown in FIG. 5.

FIG. 5 is a flow chart representing the control functions of the CPU 36, shown in the block diagram of FIG. 2; and FIG. 6 is a flow chart representing a sub-routine corresponding to an incident-and-reflected-wave peak-point determining operation carried out according to FIG. 5.

In FIG. 5, when a measurement starting operation, not shown, is carried out, the control of the CPU starts with Step S1 (hereinafter, the term "Step" is omitted). At S1, the CPU actuates the air pump 24 and operates the pressure control valve 18 and, for a blood pressure measurement, the CPU starts quick increasing of the cuff pressure Pc to the predetermined target pressure value Pcm, e.g., 180 mmHg. Then, the control goes to S2 to judge whether the cuff pressure Pc is higher than the target pressure Pcm. S2 is repeated until a positive judgment is made, while the cuff pressure Pc is quickly increased. Meanwhile, if a positive judgment is made at S2, the control goes to S3 to stop the air pump 24 and operate the pressure control valve 18 to slowly decrease the cuff pressure Pc at a low rate of from 3 to 5 mmHg/sec. Thus, S1 through S3 correspond to the cuff-pressure changing means 50 or the preliminary pressing means 50a for preliminarily pressing the skin and subcutaneous tissue of the upper arm 14 under the cuff 12 wound around, with the pressure higher than the pulse-wave detection pressure, before the cuff-pulse-wave signal SM is obtained for the measurement of augmentation index AI.

Then, at S4, the CPU reads in a one-heartbeat length of the cuff-pulse-wave signal SM supplied from the pulse-wave filter circuit 28. Subsequently, the control goes to S5 corresponding to the blood-pressure determining means 52. At S5, the CPU determines, based on change of respective amplitudes of a plurality of heartbeat-synchronous pulses of the brachial pulse wave continuously obtained at S5 during the slow decreasing of the cuff pressure Pc, a systolic blood pressure $BP_{SYS}$, a mean blood pressure $BP_{MEAN}$, and a diastolic blood pressure $BP_{DIA}$ of the subject, according to well-known oscillometric method. Then, at S6, the CPU judges whether all blood-pressure values BP have been determined at S5. S4 through S6 are repeated until a positive judgment is made at S6, while the current blood-pressure measuring operation is continued. Meanwhile, if a positive judgment is made at S6, the control goes to S7 to operate the display device 42 to display the thus determined systolic blood pressure $BP_{SYS}$, mean blood pressure $BP_{MEAN}$, and diastolic blood pressure $BP_{DIA}$ of the subject, determined at S5.

Then, the control goes to S8 corresponding to the cuff-pressure changing means 50 or the pulse-wave-detection-pressure keeping means 50b. At S8, the CPU changes and keeps, for obtaining the cuff pulse wave, the cuff pressure Pc to the pulse-wave detection pressure determined and set in advance. Subsequently, the control goes to S9 to read in a length of the cuff-pulse-wave signal SM that corresponds to at least one heartbeat of the subject. Then, the control goes to S10 corresponding to the peak-point determining means 54. At S10, the CPU carries out the peak-point determining routine shown in FIG. 6.

In FIG. 6, the control of the CPU starts with SA1 corresponding to the reference-point determining means 56. At SA1, the CPU determines, based on the waveform of the cuff pulse wave represented by the cuff-pulse-wave signal SM obtained from the cuff 12 the pressure of which is kept at the pulse-wave detection pressure, reference points on the cuff pulse wave, i.e., a rising point $t_1$ and a notch point $t_6$. For example, the reference-point determining means 56 determines, as the rising point $t_1$, a point that is subsequent to a minimum point of a heartbeat-synchronous pulse of the cuff pulse wave and has a magnitude equal to a predetermined proportion, e.g., one tenth, of an amplitude between the minimum point and a maximum point of the heartbeat-synchronous pulse, and additionally determines, as the notch point $t_6$, the first local minimum point, or the first inflection point, subsequent to the maximum point. Subsequently, the control goes to SA2 corresponding to the window determining means 58. At SA2, the CPU determines a rising-point window (i.e., a time gate) $W_1$ that starts and ends at a time $t_2$ and a time $t_3$, respectively, that are subsequent by respective prescribed times to the rising point $t_1$, and additionally determining a notch-point window (a time gate) $W_2$ that starts and ends at a time $t_4$ and a time $t_5$, respectively, that are prior by respective prescribed times to the notch point $t_6$. Subsequently, the control goes to SA3 corresponding to the fourth-order differentiating means 60. At SA3, the CPU subjects, to fourth-order differentiation, the cuff-pulse-wave signal SM obtained from the cuff 12 the pressure of which is kept at the pulse-wave detection pressure. Then, the control goes to SA4 corresponding to the incident-and-reflected-wave peak-point determining means 62. At SA4, the CPU determines, based on two zero-crossing points of the thus obtained fourth-order differentiated waveform that fall within the rising-point window $W_1$ and the notch-point window $W_2$, respectively, a peak point P of an incident-wave component of the cuff-pulse-wave signal SM, a time $t_P$ of occurrence of the point P, a peak point R of a reflected-wave component of the signal SM, and a time $t_R$ of occurrence of the point R.

Back to FIG. 5, after the peak point P of the incident-wave component of the cuff-pulse-wave signal SM, the time $t_P$ of occurrence of the point P, the peak point R of the reflected-wave component of the signal SM, and the time $t_R$ of occurrence of the point R are thus determined, the control goes to S10 corresponding to the augmentation-index determining means 66. At S10, the CPU first determines a pulse pressure (a maximum amplitude) PP of the cuff-pulse-wave signal SM obtained from the cuff 12 the pressure of which is kept at the pulse-wave detection pressure, and then determines a difference $\Delta P(=b-a)$ by subtracting a magnitude, a, of the cuff-pulse-wave signal SM at the time of occurrence of peak point $t_P$ of the incident-wave component from a magnitude, b, of the signal SM at the time of occurrence of peak point $t_R$ of the reflected-wave component. Moreover, the CPU determines, according to the relationship represented by the above-indicated Expression 1, an augmentation index AI based on the pulse pressure PP and the difference ΔP. Then, at S11, the CPU operates the display device 42 to display the thus determined augmentation index AI. Finally, at S12, the CPU operates the pressure-control valve 18 to release the cuff pressure Pc down to atmospheric pressure.

As is apparent from the foregoing description of the present embodiment, the preliminary pressing means 50a (S1 through S4) preliminarily presses, before the cuff-pulse-wave signal SM is obtained for the determination of augmentation index AI, the upper arm 14 of the subject using the cuff 12 having the pressure higher than the pulse-wave detection pressure used to press the upper arm 14 for obtaining the cuff-pulse-wave signal SM. Therefore, the water contained in the skin and subcutaneous tissue of the portion being pressed by the cuff 12 is squeezed out of the portion being pressed, so that the thickness of skin and subcutaneous tissue decreases to a value corresponding to the pressing. Since the cuff-pulse-wave signal SM is obtained in this state, the cuff-pulse-wave signal SM can enjoy a high stability, and an augmentation index determined based on the cuff-pulse-wave signal SM can enjoy a high accuracy.

Also, in the present embodiment, the preliminary pressing means 50a preliminarily presses the upper arm 14 of the subject by carrying out a predetermined number of blood-pressure measurements (in the present embodiment, one blood-pressure measurement) using the cuff. Thus, the augmentation index can be obtained simultaneously with the blood-pressure measurement.

Also, in the present embodiment, the preliminary pressing means 50a preliminarily presses the portion of the subject for a predetermined preliminary-pressing time before the cuff-pulse-wave signal SM is obtained for the determination of augmentation index AI. Thus, the water contained in the skin and subcutaneous tissue of the portion being pressed by the cuff 12 is squeezed out of the portion being pressed, so that the thickness of skin and subcutaneous tissue decreases to a value corresponding to the pressing of the cuff and, in this state, the cuff-pulse-wave signal SM is advantageously obtained for the determination of augmentation index SM.

Also, in the present embodiment, the preliminary pressing means 50a preliminarily presses, with the cuff 12, the upper arm 14 of the subject (the living person) with a pressure higher than a systolic blood pressure $BP_{SYS}$ of the subject. Thus, the water contained in the skin and subcutaneous tissue of the portion being pressed by the cuff 12 is squeezed out of the portion being pressed, so that the thickness of skin and subcutaneous tissue decreases to a value corresponding to the pressing of the cuff 12 and, in this state, the cuff-pulse-wave signal SM is obtained for the determination of augmentation index AI.

Also, in the present embodiment, the cuff-pressure changing means 50 slowly decreases, for a blood-pressure measurement, the pressure of the cuff from a pressure higher than a systolic blood pressure $BP_{SYS}$ of the subject to a pressure lower than a diastolic blood pressure $BP_{DIA}$ of the subject, and the cuff-pulse-wave signal SM is obtained, immediately after the blood-pressure measurement, from the cuff 12 having a pressure lower than the diastolic blood pressure of the subject obtained from the blood-pressure measurement. Thus, the augmentation index AI can be obtained simultaneously with the blood-pressure measurement.

Also, in the present embodiment, the blood-pressure measuring apparatus 10 having the augmentation-index determining function can be used as an arteriosclerosis inspecting apparatus. In this case, the arteriosclerosis inspecting apparatus inspects a degree of arteriosclerosis of a living subject based on an augmentation index AI determined by the augmentation-index determining means 66.

Also, in the present embodiment, the peak-point determining means 54 (S10) determines, based on the fourth-order differentiated waveform of the cuff-pulse-wave signal SM, provided by the fourth-order differentiating means 60 (SA3), the respective peak points P, R of the incident-wave and reflected-wave components of the signal SM; and the augmentation-index determining means 66 (S11) accurately determines, as the augmentation index AI, the proportion of the difference ΔP between the amplitude of the cuff pulse wave at the thus determined peak point P of the incident-wave component and the amplitude of the cuff pulse wave at the thus determined peak point R of the reflected-wave component, to the pulse pressure PP.

Also, in the present embodiment, the reference-point determining means 56 (SA1) determines the rising point of the cuff-pulse-wave signal SM, and the window determining means 58 (SA2) determines the rising-point window $W_1$ based on the rising point of the cuff-pulse-wave signal SM determined by the reference-point determining means 56. In addition, the peak-point determining means 54 determines, based on the zero-crossing point of the fourth-order differentiated waveform that falls in the rising-point window $W_1$, the peak point P of the incident-wave, component. Thus, as compared with a case in which a peak point is determined on a moderate waveform, the peak point P of the incident-wave component is more accurately determined and accordingly the augmentation index AI is more accurately determined based on the peak point P.

Also, in the present embodiment, the peak-point determining means 54 selects, as the peak point P of the incident-wave component, one of the zero-crossing points of the fourth-order differentiated waveform that fall in the rising-point window $W_1$, such that the selected one zero-crossing point has prescribed crossing direction and position as seen from the start or end point of the rising-point window $W_1$. Therefore, the peak point P of the incident-wave component is more accurately determined and accordingly the augmentation index AI is more accurately determined based on the peak point P.

Also, in the present embodiment, the reference-point determining means 56 (SA1) determines the notch point of the cuff-pulse-wave signal SM, and the window determining means 58 (SA2) determines the notch-point window $W_2$ based on the notch point of the cuff-pulse-wave signal SM determined by the reference-point determining means 56. In addition, the peak-point determining means 54 determines, based on the zero-crossing point of the fourth-order differentiated waveform that falls in the notch-point window $W_2$, the peak point R of the reflected-wave component. Thus, as compared with a case in which a peak point is determined on a moderate waveform, the peak point R of the reflected-wave component is more accurately determined and accordingly the augmentation index AI is more accurately determined based on the peak point R.

Also, in the present embodiment, the peak-point determining means 54 selects, as the peak point R of the reflected-wave component, one of the zero-crossing points of the fourth-order differentiated waveform that fall in the notch-point window $W_2$, such that the selected one zero-crossing point has prescribed crossing direction and position as seen from the start or end point of the notch-point window W₂. Therefore, the peak point R of the reflected-wave component is more accurately determined and accordingly the augmentation index AI is more accurately determined based on the peak point R.

Figure 7:
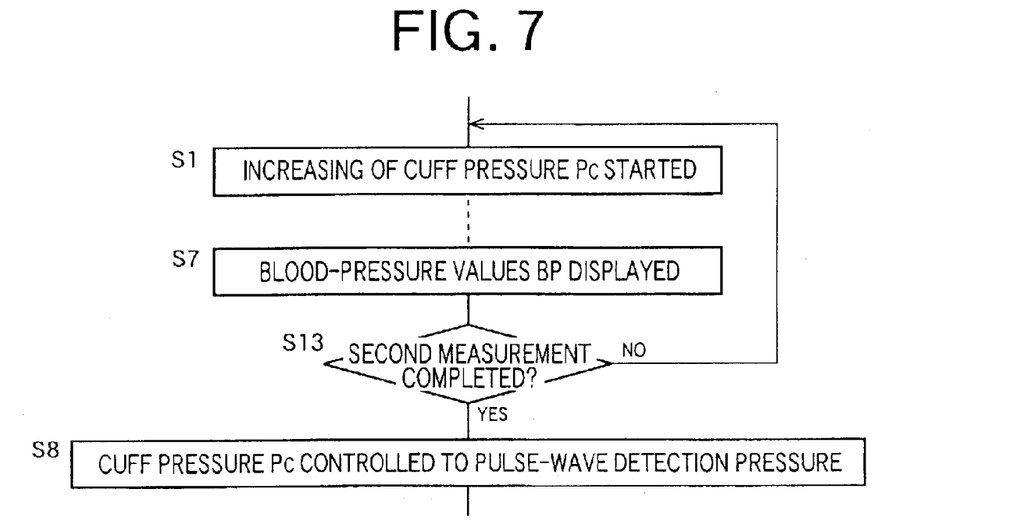
FIG. 7 is a view showing an essential portion of a flow chart which is employed by another embodiment of the present invention.

Next, another embodiment of the present invention will be described by reference to FIG. 7. The same reference numerals as used in the foregoing embodiment are used to designate the corresponding elements of this embodiment, and the description thereof is omitted. A flow chart shown in FIG. 7 differs from the flow chart shown in FIG. 5, only in that S13 where the control device 32 judges whether a second blood-pressure measurement has been completed, is provided between S7 and S8. In the present embodiment, if a negative judgment is made at S13, the control goes back to S1; and if a positive judgment is made at S13, the control proceeds with S8 so as to determine an augmentation index AI. This embodiment is useful for the case where a longer time is needed for the preliminary pressing of the upper arm 14 before the cuff-pulse-wave signal SM is obtained for the measurement of augmentation index AI.

While the present invention has been described in its preferred embodiment by reference to the drawings, it is to be understood that the invention may otherwise be embodied.

For example, in the illustrated blood pressure measuring apparatuses 10 having the augmentation-index determining function, the cuff 12 is worn the upper arm 14. However, the cuff 12 may be worn on a different body portion of the subject, such as a femoral portion or an ankle.

In the illustrated blood pressure measuring apparatuses 10 having the augmentation-index determining function, the cuff pulse wave is obtained in the state in which the cuff pressure Pc is kept at the pre-determined pulse-wave detection pressure. However, a cuff pulse wave may be obtained while the cuff pressure Pc is slowly changed, because a cuff pulse obtained through a high-performance filter is less deformed.

In addition, generally augmentation index AI is calculated according to the mathematical expression (Expression 1) wherein the denominator is pulse pressure PP. However, even in the case where the denominator is replaced with an amplitude of low-pressure-cuff pulse wave at the time of occurrence of peak point of the incident-wave component or at the time of occurrence of peak point of the reflected-wave component, a value calculated according to the thus modified expression reflects a degree of arteriosclerosis. Therefore, in Expression 1, pulse pressure PP may be replaced with amplitude of low-pressure-cuff pulse wave at the time of occurrence of peak point of the incident-wave component or at the time of occurrence of peak point of the reflected-wave component. In short, augmentation index may be defined as any value that indicates a proportion of a reflected-wave component of a cuff pulse wave to an incident-wave component of the same.

In the illustrated embodiment, the incident-and-reflected-wave peak-point determining means 62 determines, as the peak point P of the incident wave, the first zero-crossing point of the fourth-order differentiated waveform that falls in the rising-point window W₁ and where the waveform crosses zero in a direction from a positive area to a negative area, and additionally determines, as the peak point R of the reflected wave, the first zero-crossing point that falls in the notch-point window W₂ and where the waveform crosses zero in a direction from the negative area to the positive area. However, the position and direction of each zero crossing may be changed depending upon the manner in which the rising-point window W₁ and the notch-point window W₂ are determined and the manner in which the fourth-order differentiation is applied to the cuff pulse wave.

In the illustrated embodiment, the preliminary pressing means 50a utilizes the cuff-pressure control related to the measurement of blood pressure, for carrying out the preliminary pressing of the upper arm 14 before the collection of the cuff-pulse-wave signal SM for the measurement of augmentation index AI. However, the preliminary pressing means 50a may be one which performs a suitable time or times of preliminary-pressing operation or operations using a suitable pressure, independent of the measurement of blood pressure. In the latter case, the augmentation-index measuring apparatus may not be built in the blood-pressure measuring apparatus 10.

In the illustrated embodiment, the peak-point determining means 54 determines the peak point P of the incident wave and the peak point R of the reflected wave, based on the zero-crossing points on the fourth-order differentiated waveform of the cuff-pulse-wave signal SM. However, respective peak points of an incident wave and a reflected wave may be determined on a cuff-pulse-wave signal SM obtained in a state in which the pre-determined pulse-wave detection pressure is higher than a systolic blood pressure $BP_{SYS}$ of a living subject.

It is to be understood that the present invention may be embodied with other changes, improvements, and modifications that may occur to a person skilled in the art without departing from the spirit and scope of the invention.

What is claimed is:

1. An augmentation-index measuring apparatus comprising:

a cuff which is adapted to be worn on a portion of a living subject to press said portion;

an augmentation-index determining means for determining an augmentation index of the subject based on a cuff pulse wave obtained from the cuff; and a preliminary pressing means for preliminarily pressing, before the cuff pulse wave is obtained for the determination of the augmentation index, the portion of the subject using the cuff having a pressure higher than the pulse-wave detection pressure of the cuff.

2. An apparatus according to claim 1, wherein the preliminary pressing means preliminarily presses the portion of the subject by carrying out a predetermined number of blood-pressure measurements using the cuff.

3. An apparatus according to claim 1, wherein the preliminary pressing means preliminarily presses the portion of the subject for a predetermined preliminary-pressing time before the cuff pulse wave is obtained for the determination of the augmentation index.

4. An apparatus according to claim 1, wherein the preliminary pressing means preliminarily presses the portion of the subject with a pressure higher than a systolic blood pressure of the subject.

5. An apparatus according to claim 1, wherein the preliminary pressing means finishes the preliminary pressing of the portion of the subject within five minutes before commencement of the obtaining of the cuff pulse wave for the determination of the augmentation index.

6. An apparatus according to claim 1, further comprising a cuff-pressure changing device which changes, for a blood-pressure measurement, the pressure of the cuff from a pressure higher than a systolic blood pressure of the subject to a pressure lower than a diastolic blood pressure of the subject, wherein the cuff pulse wave is obtained, after the blood-pressure measurement, from the cuff having a pressure lower than the diastolic blood pressure of the subject obtained from the blood-pressure measurement.

7. Use of the augmentation-index measuring apparatus according to claim 1, for inspecting an arteriosclerosis of the subject.

* * * * *